US011103724B2

(12) United States Patent
Powell

(10) Patent No.: US 11,103,724 B2
(45) Date of Patent: Aug. 31, 2021

(54) PHOTO-TREATMENT DEVICE

(71) Applicant: Patrick Kenneth Powell, Farmington Hills, CT (US)

(72) Inventor: Patrick Kenneth Powell, Farmington Hills, CT (US)

(73) Assignee: ARBOR GRACE, INC., Detroit, MI (US)

( * ) Notice: Subject to any disclaimer, the term of this patent is extended or adjusted under 35 U.S.C. 154(b) by 343 days.

(21) Appl. No.: 15/861,979

(22) Filed: Jan. 4, 2018

(65) Prior Publication Data

US 2018/0185664 A1 Jul. 5, 2018

Related U.S. Application Data

(60) Provisional application No. 62/442,009, filed on Jan. 4, 2017.

(51) Int. Cl.
*A61N 5/06* (2006.01)

(52) U.S. Cl.
CPC ............ *A61N 5/062* (2013.01); *A61N 5/0621* (2013.01); *A61N 5/0614* (2013.01); *A61N 2005/0638* (2013.01); *A61N 2005/0666* (2013.01)

(58) Field of Classification Search
CPC ...... A61N 5/06; A61N 5/0613; A61N 5/0614; A61N 5/0616; A61N 5/062; A61N 5/0621; A61N 2005/0635; A61N 2005/0636; A61N 2005/0637; A61N 2005/0638; A61N 2005/0639; A61N 2005/065; A61N 2005/0651; A61N 2005/0654; A61N 2005/0658; A61N 2005/0662; A61N 2005/0664; A61N 2005/0665; A61N 2005/0666; A61N 2005/0667
USPC ........... 607/88–91, 93, 94, 96, 100; 128/898
See application file for complete search history.

(56) References Cited

U.S. PATENT DOCUMENTS

| 3,877,437 | A | * | 4/1975 | Maitan | ................ | A61N 5/0621 607/91 |
|---|---|---|---|---|---|---|
| 4,955,876 | A | | 9/1990 | Millner | | |
| 5,400,425 | A | | 3/1995 | Nicholas | | |
| 5,792,214 | A | | 8/1998 | Larsson | | |
| 5,824,023 | A | | 10/1998 | Anderson | | |
| 5,835,648 | A | | 11/1998 | Narciso, Jr. | | |
| 6,045,575 | A | | 4/2000 | Rosen | | |
| 6,464,715 | B1 | * | 10/2002 | Gysens | ................ | A61N 5/0621 200/61 |
| 6,596,016 | B1 | | 7/2003 | Vreman | | |
| 6,611,110 | B1 | | 8/2003 | Fregoso | | |
| 6,645,230 | B2 | | 11/2003 | Whitehurst | | |

(Continued)

FOREIGN PATENT DOCUMENTS

| WO | 2001014012 | 3/2001 |
|---|---|---|
| WO | 2011088121 | 7/2011 |
| WO | 2017004257 | 1/2017 |

*Primary Examiner* — Ahmed M Farah
(74) *Attorney, Agent, or Firm* — Carlson, Gaskey & Olds, P.C.

(57) ABSTRACT

A photo-treatment device includes a non-opaque treatment substrate and a radiation-collector beside the substrate. The substrate is sized for a person at which radiation is to be emitted from above the substrate. The substrate has a front surface for receiving the person thereon and a back surface. The radiation-collector captures excess radiation peripheral to the substrate and redirects the excess radiation to the back surface of the substrate.

10 Claims, 5 Drawing Sheets

(56) References Cited

U.S. PATENT DOCUMENTS

| | | | |
|---|---|---|---|
| 7,077,544 B2 * | 7/2006 | Parker | G02B 6/0021 |
| | | | 607/90 |
| 7,131,990 B2 | 11/2006 | Bansal | |
| 7,147,653 B2 | 12/2006 | Williams | |
| 7,210,817 B2 | 5/2007 | Lee | |
| 7,921,853 B2 | 4/2011 | Fiset | |
| 8,048,136 B2 | 11/2011 | Chung | |
| 8,202,307 B2 | 6/2012 | Rodrigues | |
| 8,246,666 B2 | 8/2012 | Pressler | |
| 8,512,386 B2 | 8/2013 | Pipe | |
| 8,536,667 B2 | 9/2013 | De Graff | |
| 9,604,072 B2 | 3/2017 | Brezinkski | |
| 2009/0030489 A1 | 1/2009 | Asvadi | |
| 2014/0200635 A1 * | 7/2014 | Ii | A61N 5/0613 |
| | | | 607/88 |
| 2015/0209598 A1 * | 7/2015 | Bhosale | A61N 5/0621 |
| | | | 607/90 |
| 2015/0217132 A1 * | 8/2015 | Makkapati | A61N 5/0621 |
| | | | 607/90 |
| 2018/0361171 A1 * | 12/2018 | Powell | A61N 5/0616 |

* cited by examiner

PHOTO-TREATMENT DEVICE

CROSS REFERENCE TO RELATED APPLICATION

This application claims priority to U.S. Provisional Application No. 62/442,009 filed Jan. 4, 2017.

BACKGROUND

Photo-treatment involves the emission of light or other radiation onto a subject. Such treatment is often used for medical purposes as a "photo-therapy." One example photo-treatment involves using light to reduce bilirubin in infants. Light, most typically blue light, is directed at the infant. The light is absorbed through the infant's skin and causes a photo-reaction that chemically breaks down bilirubin. Most often, photo-therapy is provided by lights or a spotlight suspended above the subject to shine light directly onto the infant.

SUMMARY

A photo-treatment device according to an example of the present disclosure includes a non-opaque treatment substrate sized for a person at which radiation is to be emitted from above the non-opaque treatment substrate. The non-opaque treatment substrate has a front surface for receiving the person thereon and a back surface, and a radiation-collector beside the non-opaque treatment substrate. The radiation-collector captures excess radiation peripheral to the non-opaque treatment substrate and redirects the excess radiation to the back surface of the non-opaque treatment substrate.

A photo-treatment device according to an example of the present disclosure includes a basket sized to receive a person at which radiation is to be emitted from above the basket. The basket has a side wall, a bottom wall, and an open top. A radiation-collection layer is adjacent the basket. The radiation-collection layer has a front, radiation-receiving surface and a back, radiation-transmitting surface, and a radiation manifold that has at least one radiation passage that has an inlet at the radiation-transmitting surface, an outlet at the side or bottom wall of the basket, and one or more reflective surfaces angled to reflect radiation received from the inlet and deliver the radiation by reflection to the outlet at the side or bottom wall of the basket.

A photo-treatment system according to an example of the present disclosure includes a radiation source operable to emit radiation onto a photo-treatment device. The photo-treatment device has a non-opaque treatment substrate sized to receive a person. The non-opaque treatment substrate has a front surface facing the radiation source and a back surface facing away from the radiation source, and a radiation-collector beside the non-opaque treatment substrate. The radiation-collector captures excess radiation peripheral to the non-opaque treatment substrate and redirecting the excess radiation to the back surface of the non-opaque treatment substrate.

BRIEF DESCRIPTION OF THE DRAWINGS

The various features and advantages of the present disclosure will become apparent to those skilled in the art from the following detailed description. The drawings that accompany the detailed description can be briefly described as follows.

DETAILED DESCRIPTION

Figure 1:
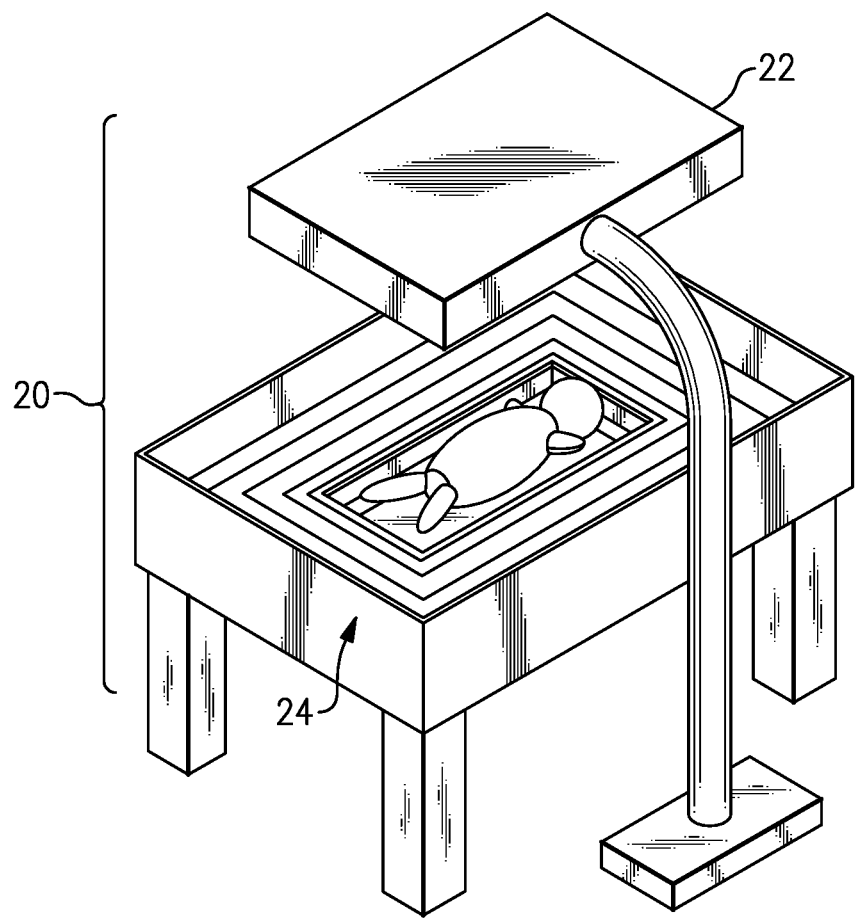
FIG. 1 illustrates a photo-treatment system that includes a radiation or light source and a photo-treatment device.

FIG. 1 illustrates a photo-treatment system 20, including a radiation or light source 22 and a photo-treatment device 24. The system 20 may be used for medical treatments, such as phototherapy to lower bilirubin levels in infants. It is to be understood, however, that the system 20 and photo-treatment device 24 are not limited to medical treatments or bilirubin treatments and may also be used for non-medical treatments (e.g., tanning, photosynthesis) and other treatments using, for example, infrared radiation, ultraviolet radiation, visible light, sunlight, or filtered radiation.

In radiation treatment the radiation must impinge on the human subject. For instance, to treat jaundice in an infant, blue light must impinge the skin of the infant in order to be absorbed and photochemically reduce bilirubin levels. Radiation that does not fall on the subject is typically wasted and does not aid in the treatment. Especially for single light/radiation sources, a significant portion of the radiation is wasted, thereby reducing effectiveness. As will be appreciated from the examples herein, the photo-treatment device 24 serves to collect radiation that does not impinge directly on the subject and redirect that radiation to a portion of the subject that is otherwise shadowed from directly receiving the radiation.

Figure 2:
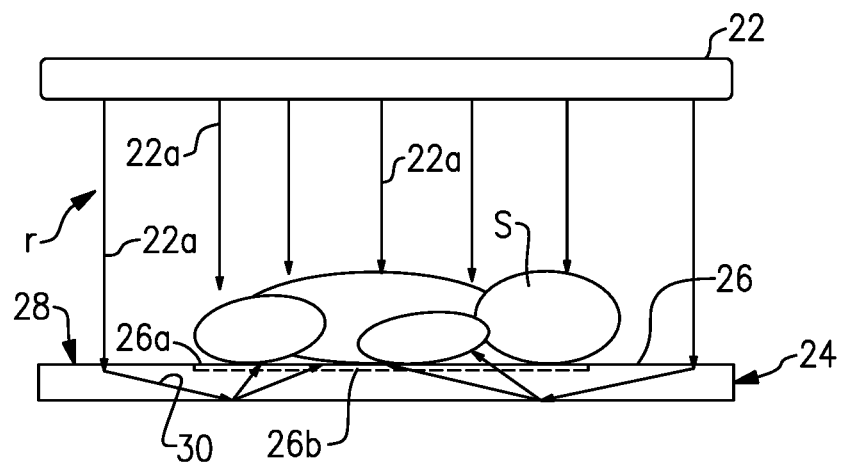
FIG. 2 illustrates selected portions of an example photo-treatment device.

As also shown in the example in FIG. 2, the radiation source 22 is operable to emit radiation 22a onto the photo-treatment device 24, which may be self-supporting or placed on an elevated platform for support (e.g., a crib or bassinet). The photo-treatment device 24 includes a non-opaque treatment substrate 26 and a radiation-collector 28 beside the non-opaque treatment substrate 26. The non-opaque treatment substrate 26 may be a flat surface or a contoured surface that is sized to receive a human, such as an infant. For instance, the non-opaque treatment substrate 26 is larger than the intended subject such that the subject fits entirely on or in the non-opaque treatment substrate 26. In further examples, the substrate has an area of at least 75 square inches.

The non-opaque treatment substrate 26 may be formed of a transparent or translucent material, such as polycarbonate, glass, clear or translucent fabrics, or the like, or wire or mesh materials that have openings that allow radiation transmission. In the case of wire or mesh, the wires may be solid/opaque, but the openings between woven wires permits transmission. The wire or mesh may thus be used to support the subject, as well as any absorbents, while thus permitting treatment. As used herein, terms such as opaque, translucent, transparent are made with reference to the type of radiation used. For instance, the substrate 26 may be transparent to visible light from the light source 22, although not necessarily transparent to other types of radiation. The substrate 26 may also be or include radiation diffusion elements and/or a filter that transmits radiation only in a selected wavelength, such as 430-490 nanometers for non-white, blue light treatment.

The substrate 26 has a front surface 26a that faces toward the radiation source 22 and a back surface 26b that faces away from the radiation source 22. A portion of the radiation 22a emitted from the radiation source 22 impinges directly on the human subject, here shown at S. This light impinges only on the side of the subject that is facing toward the radiation source 22. The area across which the radiation is projected is larger than the subject, and some of the radiation thus does not fall on the subject. In this regard, the radiation-collector 28 captures excess radiation peripheral to the substrate 26 and redirects the excess radiation by reflection, as shown at 30, to the backside 26b of the substrate 26. This redirection to the backside 26b allows the excess radiation to impinge on the shadowed side of the subject that does not directly receive radiation from the radiation source 22, including pressure-points of the subject's skin that are in contact with the substrate 26. The subject thus receives a higher percentage of the radiation from the radiation source 22, thereby increasing the dosage and enhancing the treatment. The subject also remains visible when on the photo-treatment device 24, as opposed to being obscured from vision in a hut, blanket, or the like. Moreover, the photo-treatment device does not require power or a power cord that could pose a danger to the subject.

Figure 3:
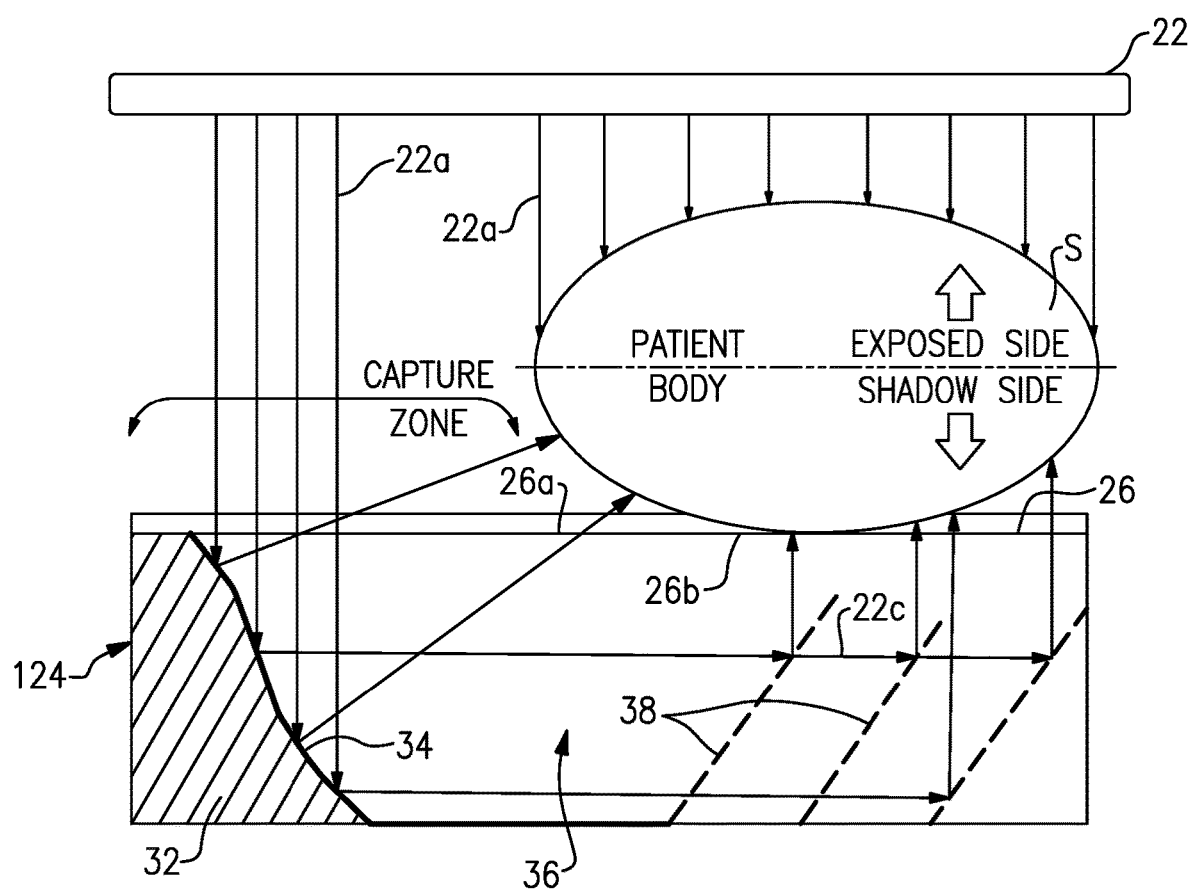
FIG. 3 illustrates another example photo-treatment device that includes a mirror surface.

FIG. 3 illustrates another example photo-treatment device 124. In this disclosure, like reference numerals designate like elements where appropriate and reference numerals with the addition of one-hundred or multiples thereof designate modified elements that are understood to incorporate the same features and benefits of the corresponding elements. The photo-treatment device 124 includes a support portion 32 that has one or more mirror surfaces 34 for reflecting the radiation 22a sideways toward the substrate 26. For example, the mirror surface 34 may be flat, faceted, convex, concave, or combinations of these that has a mirror coating disposed thereon. For instance, the mirror coating may be silver, aluminum, gold, dielectric, or a transparent top coating. Such coatings have different degrees of reflective efficiency, which may be selected with regard to performance and cost.

In this example, the mirror surface 32 reflects the radiation across a basin space 36 to one or more reflecting surfaces 38. The reflecting surfaces 38 are angled (relative to horizontal) to reflect at least a portion of the radiation received from the mirror surface 34 toward the backside 26b of the substrate 26, which transmits the radiation to the subject. Similar to the mirror surface 34, the reflecting surfaces 38 may be flat, faceted, convex, concave, or combinations of these.

As shown, the reflecting surfaces 38 may be successively arranged such that radiation 22c that does not reflect (i.e., is transmitted) from one of the reflecting surfaces 38 is then reflected by one of the next reflecting surfaces 38 in the succession. Additionally or alternatively, one or more of the reflecting surfaces 38 may be mirrored.

Figure 4A:
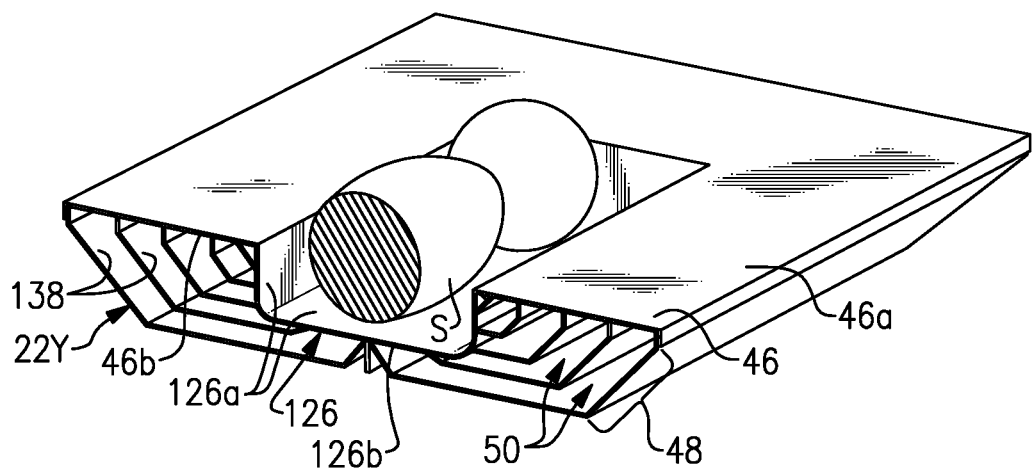
FIG. 4A illustrates a cutaway perspective view of another example photo-treatment device.
Figure 4B:
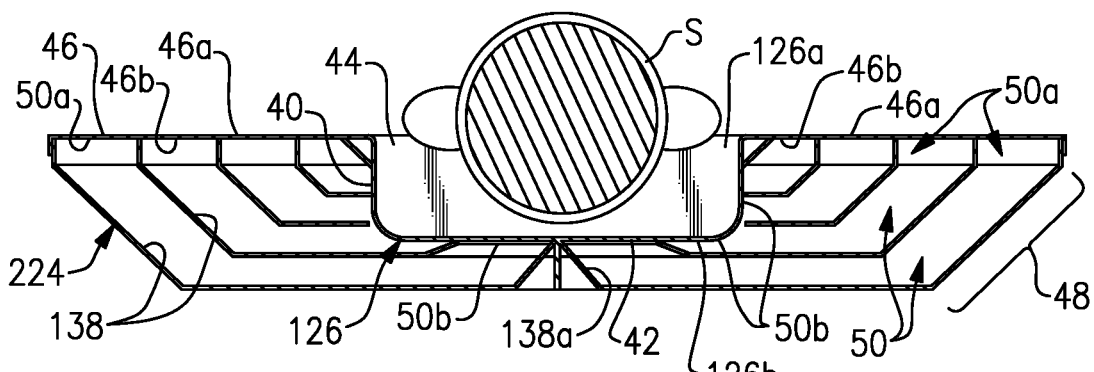
FIG. 4B illustrates a sectioned view of the photo-treatment device of FIG. 4A.

FIG. 4A shows a cutaway perspective view of another example photo-treatment device 224, and FIG. 4B shows a sectioned view of the photo-treatment device 224. In this example, the substrate is a cradle or basket 126, which, like the substrate 26, is non-opaque and sized to receive a person at which radiation is to be emitted from above the basket 126. The basket 126 has a sidewall 40, a bottom wall 42, and an open top, represented at 44, that is flush with the edges of the sidewall 40. In this case, the inside surface 126a of the basket 126 is the front side and the outside surface 126b is the backside.

The photo-treatment device 224a further includes a radiation-collection layer 46 adjacent the basket 126. The basket 126 is recessed from the radiation-collection layer 46. The radiation-collection layer 46 includes a top, radiation-collection surface 46a and a bottom, radiation-transmitting surface 46b. Radiation is received or collected at the radiation-collection surface 46a, from the radiation source 22, and is fully or partially transmitted from the radiation-transmitting surface 46b. For example, the radiation-collection layer 46 is a flat plate or sheet that is translucent or transparent. Example materials for the radiation-collection layer 46 may include glass, polycarbonate, or the like.

In this example, the radiation-collection layer 46 circumscribes the basket 126, to collect excess radiation outside the entire periphery of the basket 126. Alternatively, the radiation-collection layer 46 does not completely circumscribe the basket 126. For instance, the radiation-collection layer 46 may be only on one side of the basket 126 or around half of the basket 126.

The photo-treatment device 224a additionally includes a radiation manifold 48 underneath the radiation-collection layer 46. The manifold 48 includes at least one radiation passage 50. Each such passage 50 includes an inlet 50a at the radiation-transmitting surface 46a, an outlet 50b at the side 40 or bottom 42 wall of the basket 126, and one or more reflective surfaces 138 angled to reflect radiation received from the inlet 50a and deliver the radiation by reflection to the outlet 50b at the side 40 or bottom 42 wall of the basket 126. In one further example, one or more of the reflective surfaces 138 are mirror surfaces that reflect all or substantially all of the radiation.

Figure 5:
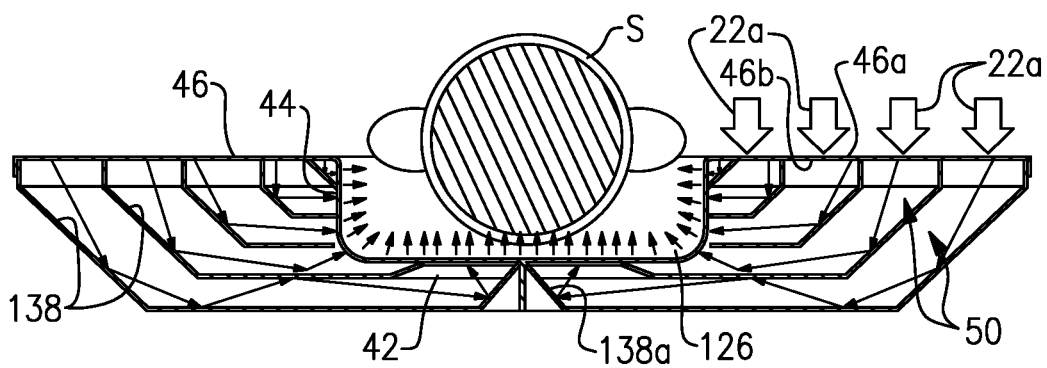
FIG. 5 illustrates the photo-treatment device of FIG. 4A during operation.

As shown in FIG. 5, during operation the radiation 22a is received or collected at the radiation-collection surface 46a of the radiation-collection layer 46 and is fully or partially transmitted from the radiation-transmitting surface 46b into the passage or passages 50. The radiation-collection layer 46 may refract the radiation, thereby "aiming" it toward the passages 50 and also facilitating collection of radiation that is received at a non-perpendicular angle to the radiation-collection surface 46a. The aiming may also reduce the number of reflections before reaching the basket 126, thus reducing energy losses from reflections. The reflecting surface or surfaces 138 reflect the radiation sideways toward the basket 126. For example, the passage or passages 50 reflect the radiation 90° such that radiation received from the vertical direction is turned horizontal. In further examples, one or more passages 50 may reflect the radiation 22a 180°. For instance, after the 90° turn, another reflecting surface 138a further reflects the radiation such that the radiation is then travelling in the opposite vertical direction from which it originated, and subsequently up through the bottom 42 of the basket 126. In a further example, the radiation-collection surface 46a may be excluded such that the radiation is received directly into the passages 50.

Figure 6:
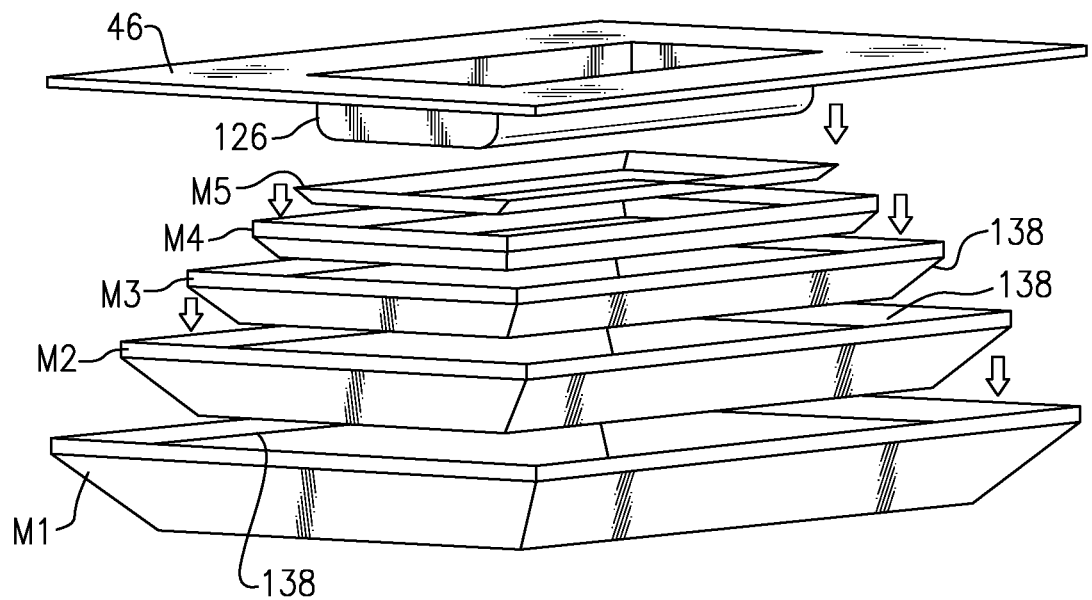
FIG. 6 illustrates an exploded view of an example photo-treatment device.

In the example shown, there are multiple passages 50 that are nested. As used herein, the term "nested" refers to similar or identically shaped structures that fit one-within-another. Thus, the passages 50 formed by the reflecting surfaces 138 are a series of nested reflectors. In this example, the outer passage 50 is the largest, and each successive passage 50 is progressively smaller to fit with the passage 50 before it. As shown in FIG. 6, the passages 50, i.e., reflecting surfaces 138, may be initially separately provided as piece-part modules M1, M2, M3, M4, and M5. Only the inside surface of module M1 is reflective, and the inner and outer sides of modules M2-M5 are reflective. A method of assembly may include stacking module M2 into module M1, followed by stacking module M3 into module M2, so on and so forth to module M5. The modules M1-M5 may be secured to one another by mechanical lock, velcro, magnetic lock, adhesive, snaps, or the like.

Figure 7:
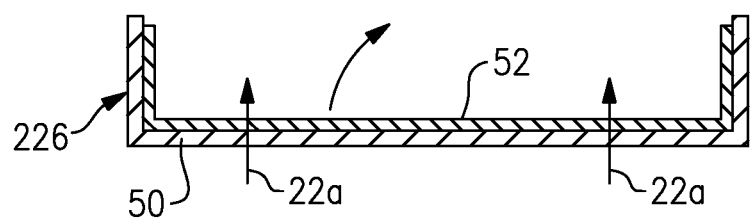
FIG. 7 illustrates an example basket and liner for a photo-treatment device.

FIG. 7 illustrates another example basket 226. In this example, the basket 226 includes a base 50 and a liner 52. Both the base 50 and the liner 52 are non-opaque such that they can transmit the radiation 22a. The liner 52 can be configured to serve one or more functions. For example, the liner 52 may be formed of fabric, paper, or the like such that it can be disposable after a single use. As used herein, disposable refers to a construction that is designed to be used once and then discarded, where the use renders the liner 52 unsanitary and thus unsuitable for use a second time. Additionally or alternatively, the liner 52 can be moisture-absorbent to wick away fluid or excrement from a subject. For instance, the liner 52 may include absorbent textiles.

Figure 8:
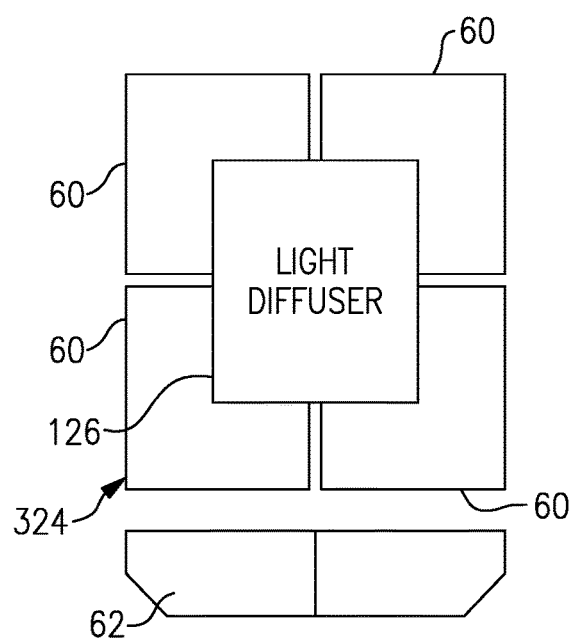
FIG. 8 illustrates another example photo-treatment device that is adjustable and is shown in an expanded state.
Figure 9:
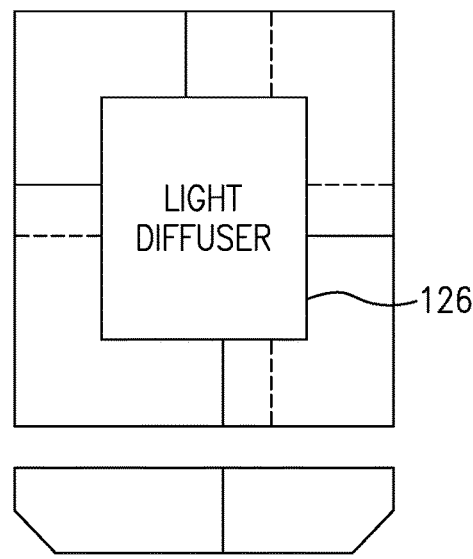
FIG. 9 illustrates the photo-treatment device of FIG. 8, in a contracted state.

FIG. 8 shows another example photo-treatment device 324. In this example, the device 324 includes two or more modules 60 (four in the illustrated example) that provide adjustability of the size of the device to fit differently sized cribs or bassinets (represented at 62). Each module 60 includes a portion of the radiation-collection layer 46 and manifold 48 and its passages 50. The modules 60 are moveable relative to one another to expand and contract the device 324. In FIG. 8, the modules 60 are in an expanded state, in order to better fit a relatively larger crib. In FIG. 9, the modules 60 are moved (e.g., manually) to overlap one another and interfit to thereby reduce the "footprint" of the device 324 to fit relatively smaller cribs. In further examples, the modules 60 provide two degrees of adjustability. For instance, the modules 60 may be moved only in the x-direction to adjust width, only in the y-direction to adjust length, or in the x-direction and y-direction to adjust width and length.

The examples herein also embody a method for photo-treatment. For instance, the method includes placing a human subject in the device 24/124/224/324, applying radiation from a radiation source, such as blue light, to the subject, collecting excess radiation that does not impinge directly onto the subject, and redirecting that radiation using the device 24/124/224/324 to a portion of the subject that is otherwise shadowed from directly receiving the radiation. As a further example, the radiation source is typically above the subject and directed downwards onto the subject. A portion of the radiation falls to the side of the subject and is collected using the device 24/124/224/324. The device 24/124/224/324 redirects the radiation onto a portion of the subject that is out of the direct line-of-sight of the radiation source. As a further example, the method may be used to increase radiation dosage by exposing a greater amount, by surface area, of the subject to the radiation at one time. That is, shadowed surfaces of the subject that are not in the direct line-of-sight of the radiation source can be exposed to the radiation at the same time as the areas that are in direct line-of-sight.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A photo-treatment device comprising:
a non-opaque treatment substrate, sized for a person, at which source radiation is to be emitted from above the non-opaque treatment substrate, the non-opaque treatment substrate having a front surface for receiving the person thereon and a back surface; and
a radiation-collector beside the non-opaque treatment substrate, the radiation-collector capturing the source radiation that is emitted from above the non-opaque treatment substrate but that impinges beside the non-opaque treatment substrate and redirecting the source radiation to the back surface of the non-opaque treatment substrate, wherein the radiation-collector includes a series of nested reflectors.

2. The photo-treatment device as recited in claim 1, wherein the non-opaque treatment substrate is translucent.

3. The photo-treatment device as recited in claim 1, wherein the non-opaque treatment substrate is a filter that transmits radiation of wavelength 430-490 nanometers.

4. The photo-treatment device as recited in claim 1, wherein the radiation-collector includes a mirror surface.

5. The photo-treatment device as recited in claim 1, wherein the radiation-collector includes a plurality of reflecting surfaces.

6. The photo-treatment device as recited in claim 1, wherein the non-opaque treatment substrate is moisture-absorbent.

7. The photo-treatment device as recited in claim 1, wherein the non-opaque treatment substrate includes a disposable non-opaque liner.

8. A photo-treatment system comprising:
a radiation source operable to emit source radiation onto a photo-treatment device, the photo-treatment device including,
a non-opaque treatment substrate sized to receive a person, the non-opaque treatment substrate having a front surface facing the radiation source and a back surface facing away from the radiation source, and
a radiation-collector beside the non-opaque treatment substrate, the radiation-collector capturing the source radiation that is emitted from the radiation source above the non-opaque treatment substrate but that impinges beside the non-opaque treatment substrate and redirecting the source radiation to the back surface of the non-opaque treatment substrate, wherein the radiation-collector includes a series of nested reflectors.

9. The photo-treatment system as recited in claim 8, wherein the radiation is non-white, blue light.

10. The photo-treatment device as recited in claim 8, wherein the non-opaque treatment substrate is a filter that transmits radiation of wavelength 430-490 nanometers.

* * * * *